United States Patent
Malinin

(10) Patent No.: US 10,004,819 B2
(45) Date of Patent: Jun. 26, 2018

(54) TISSUE ALLOGRAFT STERILIZATION METHOD

(71) Applicant: Theodore I Malinin, Key Biscayne, FL (US)

(72) Inventor: Theodore I Malinin, Key Biscayne, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 292 days.

(21) Appl. No.: 14/300,462

(22) Filed: Jun. 10, 2014

(65) Prior Publication Data

US 2015/0352235 A1    Dec. 10, 2015

(51) Int. Cl.
| | |
|---|---|
| *A61K 35/32* | (2015.01) |
| *A61L 2/00* | (2006.01) |
| *A61L 27/36* | (2006.01) |
| *A01N 1/02* | (2006.01) |
| *A01N 47/44* | (2006.01) |
| *A01N 59/00* | (2006.01) |

(52) U.S. Cl.
CPC .......... *A61L 2/0088* (2013.01); *A01N 1/0215* (2013.01); *A01N 1/0289* (2013.01); *A01N 47/44* (2013.01); *A01N 59/00* (2013.01); *A61L 27/3687* (2013.01); *A61L 27/3691* (2013.01); *A61L 2202/21* (2013.01); *A61L 2430/02* (2013.01); *A61L 2430/06* (2013.01); *A61L 2430/34* (2013.01); *Y10T 83/04* (2015.04)

(58) Field of Classification Search
CPC .............. A61L 2/0088; A61L 27/3687; A61L 27/3691; A61L 2202/21; A61L 2430/02; A61L 2430/06; A61L 2430/34; A01N 1/0215; A01N 1/0289; A01N 59/00; A01N 47/04; Y10T 83/04
See application file for complete search history.

(56) References Cited

U.S. PATENT DOCUMENTS

| | | |
|---|---|---|
| 5,095,925 A | 3/1992 | Elledge et al. |
| 5,288,462 A | 2/1994 | Carter et al. |
| 5,333,626 A | 8/1994 | Morse et al. |
| 5,336,616 A | 8/1994 | Livesey et al. |
| 5,380,826 A | 1/1995 | Castor et al. |
| 5,509,968 A | 4/1996 | Carr |
| 5,513,662 A | 5/1996 | Morse et al. |
| 5,556,379 A | 9/1996 | Wolfinbarger |
| 5,725,579 A | 3/1998 | Fages et al. |
| 5,797,871 A | 8/1998 | Wolfinbarger |
| 5,846,484 A | 12/1998 | Scarborough et al. |
| 6,024,735 A | 2/2000 | Wolfinbarger |
| 6,652,818 B1 | 11/2003 | Mills et al. |
| 2008/0188939 A1 | 8/2008 | Depaula et al. |

FOREIGN PATENT DOCUMENTS

WO    WO 9727882 A1 *    8/1997    .......... A61L 2/0094

OTHER PUBLICATIONS

Winkler, B, et al, "Graft preservation solutions in cardiovascular surgery" Interactive CardioVascular and Thoracic Surgery. (2016) 1-10. doi:10.1093/icvts/ivw056.*
Gould, G.W. New methods of food preservation. An Aspen Publication, Gaithersburg, Maryland 1999. ISBN-13: 978-0834213418 pp. 210-217.
Gould, G.W. New methods of food preservation. An Aspen Publication, Gaithersburg, Maryland 1999. ISBN-13: 978-0834213418 pp. 218-227.
Carr, J., et al.; "A feasibility study for removing tissue contamination from porous implants"; Biomed Instrum Technol 1995; 29(3):220-225.
Carpenter, EM, et al; "Effect of Hydrogen peroxide on osteoinduction by demineralized bone"; Am J Orthop 2006; 35(12):562-567.
Gollwitzer, Hans, et al; "High hydrostatic pressure for disinfection of bone grafts and biomaterials"; The Open Orthopaedics Journal; 2009; 3:1-7.
Steinhauser E et al, "Biomechanical investigation of the effect of high hydrostatic pressure treatment on mechanical properties of human bone"; J Biomed Mater Res B Appl Biomater Jan. 2006:76(1):130-5.
Clery-Barraud C et al, "Combined effects of high hydrostatic pressure and temperature for inactivation of *Bacillus anthracis* spores"; Appl Environ Microbiol 2004;70(1):635-7.
Hirn et al, "High-pressure saline washing of allografts reduces bacterial contamination"; Acta Orthop Scand 2001; 72(1): 83-85.
Hirn, et al; "Cefuroxime, rifampicin and pulse lavage in decontamination of allograft bone"; Journal of Hospital Infection (2004) 56, 198.
Malinin, T.; "Musculoskeletal tissue regeneration"; Principles of Musculoskeletal Tissue Banking; (W S Pietrzak ed) Humana Press 2008, pp. 483-508.
Park M., et al; "Oxygen Tensions and Infections: Modulation of Microbial Growth, Activity of Antimicrobial Agents, and Immunologic Responses"; Clinical Infectious Diseases. Univ. of Chicago Press, 1992.
Sale, Ajh et al, "Inactivation of Bacterial Spores by Hydrostatic Pressure"; Gen Microbiol, 1970; 60:323-334.
Sherman, W.O.; "Sterilization of Wounds, Treatment of Suppurating Wounds and Osteomyelitis (Carrel Method)"; Surg Gyn Obst. 1917; 24:255.
Watanabe T., et al, "Inactivation of Geobacillus stearothermophilus Spores by High-Pressure Carbon Dioxide Treatment"; Applied and Environmental Microbiology, Dec. 2003, p. 7124-7129.
Horst, Ludwig, et al; "Pressure inactivation of microorganisms" 1994; High Pressure Research; 12(4): 193-197.
Urist, MR, et al.; "Lipids closely associated with bone morphogenetic protein (BMP) and induced heterotopic bone formation"; Connect Tissue Res 1997; 36(1):9-20.

* cited by examiner

*Primary Examiner* — Christopher Robin Tate
*Assistant Examiner* — Douglas F White
(74) *Attorney, Agent, or Firm* — David L. King

(57) ABSTRACT

The invention is a novel method of sterilizing bone and soft tissues intended for human transplantation. In one embodiment the process includes steps of subjecting transplants to high hydrostatic pressures of aqueous fluid to which chlorhexidine gluconate or similar sterilizing chemicals have been added.

15 Claims, No Drawings

TISSUE ALLOGRAFT STERILIZATION METHOD

FIELD OF INVENTION

The invention is a novel method of sterilizing bone and soft tissues intended for human transplantation. In one embodiment the process includes steps of subjecting transplants to high hydrostatic pressures of aqueous fluid to which chlorhexidine gluconate or similar sterilizing chemicals have been added.

BACKGROUND OF INVENTION

One of the major concerns in the area of bone allograft preparation and transplantation is the removal of or inactivation of potentially contaminating microorganisms from the trabecular spaces and surfaces of the bone. Inactivation of the microorganisms including viruses is of utmost importance.

After the excision, the bone is either processed directly or it is frozen until it is further processed into small grafts under similar aseptic conditions, or under clean-room conditions. Procurement and processing of human tissues is usually performed by certified technicians under standard operating procedures for the processing of each specific bone graft. For instance, large bones such as the femur are thawed and debrided of excess tissue prior to being cut into smaller grafts.

Bone marrow includes hematopoietic progenitor cells, i.e. stem cells that will eventually differentiate into red blood cells, white blood cells, platelets, and others. These cells are rich in histocompatibility antigens that trigger immune responses. Therefore it is advantageous to have bone allograft material free of residual bone marrow. Bone grafts with minimal residual bone marrow inactivated by sterilizing agents offer additional advantages in that the removal of potential bacteria and viruses particles also reduces the chance for transmission of disease.

Conventional bone-cleaning protocols include the use of detergents, alcohols, organic solvents or similar solutes or a combination of such solutions. Common methods may use reduced or elevated temperatures, for example, between 4° C. to 65° C.

Ethanol and detergents have been demonstrated to be bactericidal toward certain bacteria, such as *Bacillus subtilis*, gram negative bacteria, for example *Yersinia enterocolitica*, gram positive bacteria, for example *Clostridia* as well as acid fast bacteria. Ethanol and detergent solutions also offer advantages of enhancing solubilization of bone marrow, reducing surface tension properties of aqueous solutions, and inactivating viruses and bacteria. However, the penetrating power of ethanol is very limited.

Typically, hydrogen peroxide is used to oxidize the colored elements within the bone marrow, as well as blood which results in a whiter, bleached appearance of the graft. However, such decolorized bone may still contain immunogenic bone marrow elements. In addition, hydrogen peroxide inhibits osteoinduction of bone allografts, an essential component of bone allograft performance.

Conventional bone-cleaning protocols do not necessarily free the grafts of bacteria, viruses and/or fungi. Viruses, bacteria, and/or fungi may also be present in the soft musculoskeletal tissues.

Cleaning of bone marrow from small bone grafts (for example, tarsals and metatarsals as small as 1-5 cm) has been described in the scientific literature and in brochures and documents made public by groups involved in the procurement and processing of human tissues. A public corporation, Cryolife, Inc. (Marietta, Ga.) promotes a bone-cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log/kilo) as well as bacteria and fungi".

Life Net Tissue Bank employs balanced and presumably optimized low concentrations of nonionic and ionic surfactants and detergents which act synergistically to lyse, solubilize and keep in solution proteins, lipids, hematopoietic progenitor cells, red blood cells, white blood cells, platelets and histocompatible antigens. The surfactants preferably include Nonoxynol-9, (a known anti-HIV agent), Brij-35 (protein solvent), Tergitol NP-40 (a lipid solvent) and IGEPAL CA 630. These surfactants are provided as micelles in presumably optimized critical micelle concentrations (CMC). They are said to dissolve bone marrow particles and/or debris, which after being washed out in the cleansing process, are reduced to a concentration below the CMC value. At that concentration level the particles and/or debris are in monomeric form (i.e., act as monomers), and can subsequently be easily removed via washing steps, leaving no detectable residues in the bone. However, the process known as "Allowash" removes the lipids not only from trabecular spaces, but intraosseous lipids as well. This is not a desirable attribute of the process, as intraosseous lipids serves as vehicles for delivering bone morphogenic proteins (BMPs) to the site.

Regeneration Technologies, Inc. employs a process termed BIOCLEANSE which depends on low-temperature chemical sterilization which destroys spores, but is said to preserve biomechanical integrity of the graft. The process utilizes hydrogen peroxide, tri(n-butyl)phosphate, betadyne-iodine mixture, TritonX-100 and other compounds. Additionally the grafts are sterilized either by irradiation or by hydrogen peroxide gas plasma method. The latter have commonly acknowledged deficiencies.

Several other methods for sterilization of tissue implants have been made public.

U.S. Pat. No. 5,380,826 relates to a method for harvesting intracellular components by exposing cells to an elevated pressure in the presence of a solvent, and then rapidly and suddenly releasing the pressure to effect disruption of the cells, the patent also discloses an apparatus for carrying out this process continuously. However, this patent neither discloses nor suggests applying the cell disruption method to allograft bone or tissue. U.S. Pat. No. 5,288,462 describes a chamber for receiving material to be sterilized by repeatedly subjecting the chamber to elevated pressures, followed by sudden release of the pressure, i.e. "explosive decompression". There is no disclosure that would allow one skilled in the art to determine, without undue experimentation, that bone could be sterilized in this apparatus.

U.S. Pat. No. 5,725,579 is directed to a method of cleaning bone by exposing the bone to a supercritical fluid. As best as can be understood from this patent, this involves exposing bone to carbon dioxide at elevated pressures, in order to solubilize lipids.

Tissue sterilization methods known in the art have undesirable attributes. Gamma irradiation, in order to ensure destruction of pathogens, such as the human immunodeficiency virus (HIV), has to be used at doses that result in tissue destruction.

Use of ethylene oxide has been found to result in implants that on intraarticular transplantation produce inflammatory responses. However, this was observed only with soft tissue allografts used for ACL replacements. The phenomenon could not be reproduced experimentally. Thus ETO sterilization of bone remains one of the most effective methods of tissue sterilization.

Standard chemical solution treatments may be effective in sterilizing surfaces with which the solutions are brought into contact. The major disadvantage is insufficient penetration to reach the inside of the tissues where pathogenic organisms may harbor. In view of these shortcomings, there is a long-felt/need for an optimized tissue sterilization process, which would incorporate the following features: Effective inactivation of a wide range of bacterial and viral pathogens; absence of graft toxicity; retention of desirable tissue characteristics, such as biomechanical strength and osteogenesis.

High hydrostatic pressure (HHP) had been proposed as a novel method of microbial inactivation while preserving biological and biomechanical properties of bone. High hydrostatic pressure offers limited microbial inactivation of common contaminating microorganisms, but its effectiveness is limited to barosensitive microorganisms and colonization. High hydrostatic pressure had been used in food processing for over 100 years. Many vegetative forms of microorganisms are impaired by hydrostatic pressures in the ranges of 300-600 MPa. However, HHP only reduces the viability of barosensitive organism, but does not obliterate all potentially pathogenic microorganisms.

Bone cleaning protocols involve many methods and cleaning solutions. These may be detergents, organic solvents, alcohol or similar solutes. Several physical methods are also employed; these include agitation, ultrasound, high pressure and others.

Many procedures combine bone cleaning with microbial deactivation. It is at times difficult to distinguish the processes. Alcohol and detergents are bactericidal to certain bacteria, but alcohol has poor penetration capacity. Wolfinbarger in U.S. Pat. No. 6,024,735 describes a method of removing bone marrow by employing a detergent having functionality of polyoxyethylene-23 lauryl ether, in a process termed Allowash. Biocleanse, as previously described, relies on (n-butyl) phosphate, betadyne, TritonX-100/TNBP and the like mixtures. Patent application 20080188939, filed Aug. 7, 2008 describes allograft purification process for cleaning bone. The first step is sonication of bone in non-ionic detergent followed by sonication in purified water. The process is said to produce bone allograft essentially free of bone marrow. The final step is the sonication of graft in alcohol, a step which deactivates many microorganisms, but is not intended to clean the bone.

In addition to sonication, physical means of cleaning bone allografts include pressurized flow of solutions, pressure lavage, vacuum shown in U.S. Pat. No. 5,513,662, high pressure washing which includes vigorous agitation, such as with a paint can shaker or high pressure liquid stream shown in U.S. Pat. No. 5,333,625. For the record, agitation with a paint can shaker had been used by the University of Miami Tissue Bank since 1972. Oscillating atmospheric pressure had been also described in U.S. Pat. No. 6,652,818.

SUMMARY OF INVENTION

The invention is a novel method of sterilizing bone and soft tissues intended for human transplantation. In one embodiment the process includes steps of subjecting transplants to high hydrostatic pressures of aqueous fluid to which chlorhexidine gluconate or similar sterilizing chemicals have been added. The aqueous solution can be isotonic, hypertonic or hypotonic. In another embodiment hypotonic solution is used to lyse red blood cells and other cells to reduce the antigenicity of the transplant concomitantly with its sterilization. In still another embodiment the bone is washed with fluid containing micro bubbles of oxygen or carbon dioxide. The invention is a cascade procedure with washing with chlorhexidine gluconate solution followed by an exposure to solutions releasing hypochlorous acid.

The invention relates to a novel method of sterilization or disinfection of tissue allografts, xenografts, and autografts prior to transplantation into recipients for therapeutic purposes. In one embodiment, the method includes washing of the transplants under high hydrostatic pressure with aqueous antimicrobial liquids. The method assures penetration of biocides into treated tissues resulting in inactivation of pathogens, microorganisms, viruses, fungi and other biologic contaminants. The method likewise can inactivate and lyse cells resulting in the reduction of antigenicity of the grafts, while maintaining the integrity and biologic properties of the grafts. The aqueous solutions administered under high hydrostatic pressures include chlorhexidine gluconate, chloramine-T, Dakin solution, and similar solutions which release hypochlorous acid as well as other germicidal halogen compounds or a combination thereof The cascade method of employing sequentially two types of germicidal solutions with intermittent washing with hypotonic and isotonic solutions assures the preparation of aseptic biologic grafts with retention of their original properties.

The invention provides a process whereby tissues from a donor are taken through a sequential process of cleaning and sterilization rendering them safe and effective on transplantation into human recipient. The process, termed UMTBAL-LOSAFE preserves natural ingredients and basic biologic properties of the tissues treated. The capacity of bone to induce osteogenesis is preserved. Biomechanical properties of the tissue grafts remain unaltered. In one embodiment the invention comprises a process wherein high hydrostatic pressure is used to permeate the treated tissues with sterilizing solutions, of which at least two are used in each cycle. In another embodiment aqueous solutions which are either oxygenated or carbonated under pressure are used to produce effervescence which aids in washing the grafts. The process essentially comprises the following steps. Cleaned and/or debrided graft material is used as the starting material: Material is placed in a sterile metal container and inspected to determine whether or not additional cleaning is necessary. If such is the case, additional cleaning is performed with sterile water directed through a jet stream. Jet stream may also be used to cut bone and cartilage. Cleaned allografts are then placed into a high-hydrostatic pressure chamber filled with a 0.5 to 5% solution of chlorhexidine gluconate. The grafts may be placed directly into the sterilizing medium or they can be sealed in pliable containers with chlorhexidine gluconate solution. The latter are then placed into a high hydrostatic pressure solution. The high-hydrostatic pressure, from 100 to 400 MPa is applied and maintained for a predetermined period. The pressure is then released and the grafts are washed with carbonated or oxygenated aqueous solution. Next the grafts are placed into a full strength, half strength or quarter strength Dakin solution, and are again subjected to the high-hydrostatic pressure. Upon release of pressure the grafts are washed with oxygenated or carbonated saline solution and are frozen, freeze-dried or preserved by other means.

Definitions

The below definitions serve to provide clear and consistent understanding of the claims and specifications including scope to be given such terms.

Agitation. By term "agitation" is intended any method of shaking, mild and vigorous. Shaking can be carried out in a solution, and in high pressure or atmospheric pressure environment.

UMTBALLOSAFETM process. By the term "UMTBALLOSAFE" is intended the sequential method of washing and sterilizing bone, cartilage or soft tissue grafts. Examples of UMTBALLOSAFE process include applications of 0.5 to 5% solutions of chlorhexidine gluconate, chloramine T, Dakin solution, and other compounds singly or in combination capable of producing hypochlorous acid. These solutions as well as water and saline can be oxygenated or carbonated at high pressure. These solutions can be employed at high hydrostatic pressures or at atmospheric pressures.

Blood Deposits. By the term "blood deposits" is intended to denote blood cells including red blood cells, white blood cells, platelets and other cells circulating in the blood, as well as contaminates of microbial, viral or fungal nature which might be circulating in the blood.

Bone Graft. By the term "bone graft" is intended any bone or piece of bone obtained from a human donor, living or non-living (allograft bone) bone from an animal (xenograft bone) or bone from the human recipient (autograft bone).

Bone Marrow or Bone Marrow Elements. By the term "bone marrow" or "bone marrow elements" is intended for the purposes of the present invention cellular hemopoietic tissue found in the trabecular bone. This harbors "antigen presenting cells" and may also harbor bacterial, fungal or viral contaminants.

Decontaminating Agent or Sterilizing Agent. By the term "decontaminating agent" or "sterilizing agent" is intended one or more agents which inactivate or destroy any infectious material, potentially present in the bone, cartilage or soft tissue grafts, such material including, but not limited to bacteria, viruses or fungi. Decontaminating or sterilizing solutions for the purposes of the present invention include, but are not limited to chlorhexidine gluconate, Dakin solution, chloramine T, hydrogen peroxide and alcohols.

Essentially Free From. By the term "essentially free from" is intended for the purposes of the present invention a bone graft, cartilage graft or soft tissue graft has no detectable bacterial, viral or fungal particles as might be revealed using detection means known in the art at the time of filing of this application.

Essentially Intact Bone, Cartilage and Soft Tissue Grafts. By the term "essentially intact bone, cartilage and soft tissue grafts" is intended for the purposes of the present invention any intact bone including for example the tibia, radius and femur and/or any other bone which can be removed with minimal cutting of such bone, for example one half of the humerus, femur or tibia or designated as distal or proximal halves.

Essentially Intact Cartilage. By the term "essentially intact cartilage" is meant for the purposes of the present invention the epiphyseal ends of bones covered with an intact cartilage cap.

Essentially Intact Tendon. By the term "essentially intact tendon" is meant for the purposes of the present invention the major portion of a tendon such as tibialis anterior tendon, or an Achilles or patella ligaments divided longitudinally.

High Hydrostatic Pressure. By the term "high hydrostatic pressure" also known as gravitational pressure is intended for the purposes of this invention the hydrostatic pressure generally, but not limited to of about 100-600 MPa, transmitted through liquid medium. High Hydrostatic Pressure System. By the term "high hydrostatic pressure system" is intended for the purposes of this invention a high hydrostatic pressure vessel and its closure.

Ultra-high Water Pressure. By the term "ultra-high water pressure" is intended for the purposes of this invention pressurizing of water to ultra-high pressures and focusing it into a high velocity stream.

Carbonation. By the term "carbonation" for the purposes of the present invention is intended dissolving of carbon dioxide in an aqueous solution under pressure.

Oxygenation. By the term "oxygenation" for the purposes of the present invention is intended dissolving of oxygen in an aqueous solution under pressure.

DETAILED DESCRIPTION

The present invention does inactivate bacterial microorganisms, fungi and viruses. It allows for synergistic action of sequential chemical inactivation with HI=IP.

Current data clearly shows that bone can prevent sterilizing solutions from reaching microorganisms embedded in it. However, HHP enhances penetration of sterilizing solutions into interstices of bone and other tissues. The present invention calls for the delivery of sterilizing solutions of compounds such as chlorhexidine gluconate, chloramine T, Dakin solution, triclocarban, octenidine dihydrochloride and others. For example tissue allografts are placed into pliable containers filled with germicidal fluid and sealed under vacuum with plastic foil. The latter is then placed into a chamber to which pressure is applied. Pressurization is applied to 200-600 MPa. Decompression is performed at about 10 MPa/s.

Several apparatuses which produce high hydrostatic pressures are available. Most, employed in the laboratory studies, have small chambers. No pressure apparatus designed for sterilization of bone and soft tissue allografts is available. Therefore such an apparatus is one embodiment of the present invention. The apparatus has a capacity of 5 gallons. It consists of 4 parts. A cylindrical section (1) is constructed of stainless steel and can be sterilizable with steam. It is attached to metal plates (1, 2) by steel bolts (3). A unique feature of the apparatus is in which 3 parts of the chamber are joined together avoiding use of pressure-tight seals. Instead metal-to-metal joints are used. The stresses along the circular lines of contact are great enough to cause plastic deformation of metal thus avoiding leakage.

At the turn of the last century the ability of high hydrostatic pressure to preserve dairy products and to denature egg albumin had been discovered. Since then a number of studies dealing with biologic effects of high hydrostatic pressure had been conducted. Majority were applicable to the food industry. Usually high hydrostatic pressure treatment is carried out semi-continuously. The packaged product is inserted into a cylindrical metal vessel and pressure is increased directly or indirectly. For direct compression, the medium inside the vessel is pressurized by a piston driven at its large diameter. The pressure is transmitted into the vessel by a small diameter high-pressure end of the piston. High pressure is determined by multiplying the low pressure by the ratio of two piston diameters. For indirect pressurization, a high pressure intensifier is used to pump the medium from the reservoir into a closed high-pressure vessel.

Most high hydrostatic pressure systems utilize a second container which is placed into the pressure chamber. The product to be subjected to high hydrostatic pressures is in turn placed into that container. The desirable characteristic for packaging materials for high-hydrostatic pressure treatment includes pressure tightness, flexibility and heat sealability.

Due to a volume decrease upon pressurization, any phenomenon such as chemical reactions, phase transition, molecular configuration and other changes that are accompanied by a volume reduction are enhanced by high hydrostatic pressure.

The compression of the pressure medium and the product within it is accompanied by the temperature elevation of about 2-3° C. per 100 MPs. However, isothermic conditions can be maintained in the high hydrostatic pressure apparatus by temperature control which would dissipate heat on compression and supply heat during decompression.

HPP is a new technology for allograft preparation, 215 liter apparatus is available commercially. Although HPP has been used for sterilization of foods, and the process had been shown to inactivate *Bacillus anthraces* spores, its use in the present invention is to enhance penetration of sterilizing solutions into bone and tissue allografts. This approach is amplified by the fact that when contaminated bone was exposed to HHP alone disinfection of bone allografts was limited by the baroprotective properties of bone.

A major goal in the area of bone allograft technology is the effective and safe removal of bone marrow, blood, blood clots and other biologic fluids from the allografts.

For bone allografts, bone is ideally removed under aseptic conditions in an operating room environment. The bone so removed can be kept at hypothermia and processed within five days or it can be frozen and processed later. Each bone and a hemi-joint can be prepared as an entire structure, partial structure or it can be cut into smaller pieces. Processing includes removal of bone marrow, blood and extraosseous lipids. Removal of the bone marrow is desirable because bone marrow contains so called antigen presenting cells which elicit immune response in the host into whom they are transplanted.

With regard to bone cleaning, the present invention does not utilize any of the previously described methods, but depends on first cleaning of bone by saline wash which was shown to be effective in removing bacteria from bone allografts , followed by washing with a modified ultra-high pressure, high velocity water stream. When intensified the same water jet can be used to cut bone. This can be accomplished by employing either direct-drive or crankshaft pumps. Cutting of bone with water jet is achieved with accuracy without leaving any frayed edges or burns.

After the bone is washed, it is placed into a high hydrostatic pressure chamber in an oxygenated water or saline solution containing 0.5 to 5% solution of chlorhexidine gluconate. Hyperoxia and hyperbaric oxygen increase antimicrobial effect of antimicrobial agents. When the pressure is reduced the solution becomes effervescent. Effervescence will further aid in the washing of treated allografts.

An alternative to oxygenation of the washing solution is carbonation, a commonly practiced art in many commercial applications. High pressure CO2 treatment has been shown effective in inactivating a number of bacterial spores. Release of pressure would likewise produce effervescence.

After treatment with chlorhexidine gluconate, the allografts are washed in saline again under high hydrostatic pressure to remove residuals of chlorhexidine gluconate and are then placed in a solution which produces hypochlorous acid. The solution of choice is full strength freshly prepared Dakin solution. As an alternate Chloramine T, an effective biocide can be also used. The activity of Dakin solution depends on the release of hypochlorous acid, a weak and unstable acid which occurs only in solutions and is an effective oxidizer and disinfectant. The Dakin solution must be prepared with precision. It must be free of caustic alkali and it must contain only 0.45 to 0.50% of hypochloride. Boric acid (0.4% w/v) was originally added to Dakin solution. The solution is prepared from bleaching powder (a mixture of calcium hydroxide, calcium chloride and calcium hypochloride). To make 10 liters of the solution 200 gm of bleaching powder, 100 gm of sodium carbonate and 80 gm of sodium bicarbonate are dissolved in the same. If boric acid is used, 40 gm of the same is added. The ingredients are left in the solution overnight. The solution is then filtered and tested.

II. Cleaning Compositions

The bone cleaning composition is performed in a standard fashion prior to initiation of sterilization procedure. If bone marrow elements within the cancellous bone have not been removed entirely, the bone is washed again in accordance with the present invention. The advantages of the techniques employed in the present invention are that bone is not exposed to harsh chemicals such as alcohols, chloroform, detergents and similar compounds. Intraosseous lipids and other associated lipids are essential to the transport of BMP. The cleaning process employed in the present invention does not extract lipids as would exposure to alcohol, chloroform and other lipid solvents.

If additional cleaning is required according to the present invention, the grafts are washed with a water jet system adjusted to below the cutting capacity of the water jet.

In pure water jet, the water stream can erode the material and thus be used for cutting. If the pressure is set lower, the water jet can be used for removing blood as well as bone marrow residues. The system is based on the capacity of the pump. The pump pressurizes the water and delivers it continuously to the pressure head which can be used as a surface cleaner or a cutting instrument, depending on the pressure settings. Water stream with the pressure set below the cutting pressure is very effective in cleaning the bone and soft tissue grafts of bone marrow and blood residues rendering them essentially free of these.

III. Sterilization Compositions

The bone, cartilage and soft tissue sterilization compositions according to the present invention result in deactivation and removal of bacteria, fungi and viruses which might potentially contaminate these structures. The components of the invention are non-toxic and leave no residual in the treated tissues.

Two major sterilizing agents employed in the present invention are chlorhexidine gluconate solution and the Dakin solution. The solutions, singly or in sequence employed in the UMTBALLOSAFE process are applied under high-hydrostatic pressure. Hydrostatic pressure, the pressure at point in a fluid at rest due to the weight of the fluid above it, also known as gravitational pressure, had been used for inactivation of microorganisms. Although high-hydrostatic pressures (HHP) have been reported to inactivate bacterial spores such as those of *Bacillus anthraces* testing it on infected bone specimens showed that not all microorganisms are inactivated by HHP. Therefore, for the purposes of this invention HHP alone cannot be used. However, when HHP is used in combination with germicidal solution(s) it assures the penetration of the same throughout the tissues treated and produces inactivation of all potentially contaminating microorganisms. Therefore the first step in the UMTBALLOSAFE process is washing of the grafts, using high pressure jet if necessary. The second step is 0.5 to 5% solution of chlorhexidine gluconate in a pressure chamber with pressures ranging but not limited to 50 to 400 MPa. Chlorhexidine gluconate is a cationic surfactant. It is a biguanide derivative. It is commonly used in the treatment of gingivitis and a skin and wound antiseptic. Chlorhexidine preparations have been used extensively in burns for cleansing and antisepsis. Chlorhexidine gluconate antimicrobial activity is directed mainly towards vegetative gram-positive and gram negative bacteria. It is inactive against bacterial spores unless combined with heat or HHP. For these reasons the grafts are exposed to a second solution which inactivates spores. Chlorhexidine is effective against viruses with a lipid component in their coats. HIV is known to be one of the enveloped viruses and is therefore sensitive to the action of chlorhexidine. To achieve microbial inactivation exposure for as little as 10 min is sufficient.

The third step in the UMTBALLOSAFE process is washing of the grafts again under pressure. Either carbonated or oxygenated solution is used to achieve this. After the washing is completed the grafts are immersed into Dakin solution (Fourth step in the ALLOSAFE process) which destroys bacterial spores, including those of Anthrax. The active principle of Dakin solution as well as that of Dakin solution to which boric acid had been added (Eusol) is hypochlorous acid. Hypochlorous acid is weak, unstable acid and hence it cannot be prepared as such. In nature, hypochlorous acid is found in neutrophils, which allows neutrophils to kill bacteria. Dakin solution must be neutralized to prevent it from being alkaline and caustic. For the purposes of this invention Dakin solution can be prepared from bleaching powder, by electrolysis and from sodium hypochlorite. Dakin solution loses its activity after about one hour if it is in contact with biologic material. Therefore, if it is desired to increase the exposure time to Dakin solution it is changed every hour. As an alternative to Dakin solution, chloramine T can be used for the purposes of the present invention. Chloramine T is an N-chloro tosylamide salt. It is an n-chlorinated and N-deprotonated sulfonamide, and is a biocide and a mild disinfectant. As an N-chloro compound it contains electrophilic chlorine and is comparable to O-chlorinated sodium hypochlorite. Its advantage is that it is almost neutral with a pH of around 8.5.

The fifth step in the UMTBALLOSAFE process is washing of the grafts after exposure to Dakin solution. The washing is done with saline, Tissue-Sol or lactated Ringer's solution so the grafts can be exposed to isotonic environment before these are frozen, freeze-dried or preserved by other methods.

An additional embodiment is the treatment of the grafts after the five steps disclosed in this invention is by one or more natural antimicrobials from plants. According to Mitscher (Recent Advances in Phytochemistry 1975; Vol 9, Plenum Press) plants can be the sources of antimicrobial agents. Their structure and mode of action are different from the conventionally derived antibiotic agents. Therefore, they do not pose a problem with emerging microbial resistance to antibiotics.

For the purposes of this invention the compounds used for additional treatment of sterilized grafts are phytoalexins, organic acids, essential oils and phenolics; pigments and related compounds.

The above description allows for a novel method for producing grafts of bone, cartilage or soft tissues suitable for transplantation into a human using high hydrostatic pressure for delivery of one or more sterilizing solutions including chlorhexidine gluconate, Dakin solution, chloramineT and/ or other solutions generating hypochlorous acid. In one embodiment, the treating of such grafts is with chlorhexidine gluconate under high hydrostatic pressure, preferably with 0.5 to 5% chlorhexidine gluconate.

This achieves a bone, cartilage or soft tissue graft suitable for transplantation into humans comprising of the sterilized graft produced by the process wherein the graft is essentially free from bacterial, fungal, viral or parasitic contamination.

In a second embodiment, the method of producing bone, cartilage and soft tissue graft suitable for transplantation into a human uses an application of Dakin solution and/or other compounds which produce hypochlorous acid under high hydrostatic pressure and further can include washing of said washed and sterilized grafts with distilled water or sterile saline.

Preferably, a method for producing prewashed bone, cartilage and soft tissue graft with sterile water or sterile physiologic saline with velocity high pressure stream wherein the graft is prewashed with sterile physiologic saline with high velocity high pressure stream. Additionally, a method for cutting prewashed bone, cartilage or soft tissue suitable for transplantation into a human with a "Jet Set" or other high velocity high pressure, focused water jet stream.

Alternative methods for washing bone, cartilage and soft tissue graft use solutions oxygenated under pressure or carbonated under high pressure.

The invention includes a method of producing bone, cartilage or soft tissue grafts suitable for transplantation into a human comprising; washing said grafts under high pressure to produce a cleaned graft; treating said graft with one or two decontaminating solutions under high hydrostatic pressure; washing said grafts with water or saline solutions oxygenated under high hydrostatic pressure; washing said grafts with water or saline solutions carbonated under high hydrostatic pressure, wherein such washing and sterilizing treatments comprise one or more soaking, treatment at high pressure with sterilizing solutions and washing in solutions producing effervescence.

What is claimed:

1. A method for producing a bone graft suitable for transplantation into a human from cadaver bone, the method comprising the steps of:
   (a) initially washing the cadaver bone;
   (b) exposing the washed cadaver bone to a jet stream from a water jet system, which has been adjusted below a cutting capacity of the water jet system, to form a jet stream-washed bone graft;
   (c) delivery of one or more sterilizing solutions containing chlorhexidine gluconate, Dakin solution, chloramineT and/or other solutions generating hypochlorous acid to the jet stream-washed bone graft using a high pressure chamber having a high hydrostatic pressure so as to achieve microbial inactivation of the bone graft;
   (d) re-washing the microbial inactivated bone graft under high hydrostatic pressure in the range of 100-600 MPa to remove residuals of the one or more sterilizing solutions; and
   (e) immersing the re-washed bone graft in Dakin solution or other solution producing hypochlorous acid at normal atmospheric pressure.

2. The method of claim 1, wherein in step (c) the bone graft is treated with a 0.5% to 5% solution of chlorhexidine gluconate.

3. The method of claim 1, further comprising washing the bone graft with distilled water after step (e).

4. The method of claim 1, further comprising washing the bone graft with distilled water after step (e).

5. The method of claim 1, wherein in step (c) the sterilizing solution contains chlorhexidine gluconate and the high hydrostatic pressure is in the range of 50-400 MPa.

6. The method of claim 5, further comprising washing the bone graft with distilled water after step (e).

7. The method of claim 5, further comprising washing the bone graft with distilled water after step (e).

8. The method of claim 1, wherein in step (c) the sterilizing solution contains Dakin solution and/or other compounds which produce hypochlorous acid under high hydrostatic pressure, and wherein the high hydrostatic pressure is in the range of 50-400 MPa.

9. The method of claim 8, further comprising washing the bone graft with distilled water after step (e).

10. The method of claim 8, further comprising washing the bone graft with distilled water after step (e).

11. The method of claim 1, wherein in step (b) the jet stream from the water jet system comprises a jet stream of sterile water or sterile physiologic saline.

12. The method of claim 11, wherein in step (b) the jet steam comprises sterile physiologic saline.

13. The method of claim 11, further comprising cutting the prewashed bone with a high pressure focused water jet stream, the high pressure being adjusted to cut bone in the range of 100 to 600 MPa.

14. The method of claim 1, wherein in the step (d) the re-washing under high hydrostatic comprises re-washing with oxygenated or carbonated solutions, under high pressure in the range of 100 to 600 MPa.

15. The method of claim 14 wherein the solutions are carbonated solutions.

* * * * *